United States Patent [19]  [11] 3,971,803
Rosenberger et al.  [45] July 27, 1976

[54] 3-HYDROXYBENZYL-OXADIAZOLONE AND -THIADIAZOLONE DERIVATIVES

[75] Inventors: Siegfried Rosenberger, Riehen; Kurt Schwarzenbach, Pfeffingen, both of Switzerland

[73] Assignee: Ciba-Geigy Corporation, Ardsley, N.Y.

[22] Filed: May 15, 1974

[21] Appl. No.: 469,988

[30] Foreign Application Priority Data

May 21, 1973 Switzerland............... 7190/73

[52] U.S. Cl................. 260/307 A; 260/45.8 N; 260/45.8 SN; 260/45.8 NZ; 260/302 D; 260/302 S; 260/302 SD; 260/455 A; 260/570.9; 260/623 D
[51] Int. Cl.$^2$........................... C07D 271/10
[58] Field of Search...... 260/307 A, 302 SD, 302 D, 260/302 H

[56] References Cited
UNITED STATES PATENTS
3,836,539  9/1974  Boesch............................ 260/307 A

*Primary Examiner*—Raymond V. Rush
*Attorney, Agent, or Firm*—Charles W. Vanecek

[57] ABSTRACT

1,3,4-Oxadiazolones and 1,3,4-thiadiazolones substituted in position 3 by sterically hindered p-hydroxybenzyl and in position 5 by mono- or divalent hydrocarbon or by alkoxy or alkylthio and the 2-thiono analogs of the above defined compounds can be synthesized by hydroxybenzylation of the corresponding 3-hydrogen compounds, for instance, with formaldehyde and a sterically hindered phenol. Intermediately the 3-hydroxymethyl compounds are formed which may be isolated. The hydroxybenzylation may further be accomplished by means of the corresponding hydroxybenzyl halides, amines or dithiocarbaminates. The products are stabilizers for organic polymers to protect them against thermo-oxydative degradation. They show an outstanding stability against discoloration.

6 Claims, No Drawings

3-HYDROXYBENZYL-OXADIAZOLONE AND -THIADIAZOLONE DERIVATIVES

The present invention relates to new 3-hydroxybenzyloxadiazolones and their sulphur analogues, their manufacture, their use for stabilising organic material and the organic material stabilised with their aid.

It is known to add derivatives of sterically hindered phenols as stabilisers of organic polymers against their thermooxidative degradation or against their aging by light. Many of these phenolic derivatives suffer from the disadvantage that they discolour the organic polymer objectionably either even or incorporation or on exposure to light or on contact with industrial flue gases or on contact with hot water, and this greatly restricts their industrial usefulness. New compounds have now been found which, surprisingly, are not only outstandingly suitable for stabilising organic materials, especially organic polymers, but also remain colourless under the abovementioned conditions and protect the organic material against discolouration. This means that the new compounds stablise the organic material both against degradation and against discolouration.

The new compounds according to the invention correspond to the formula I

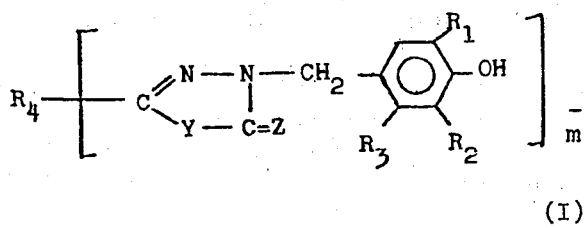

(I)

wherein $R_1$ denotes alkyl, cycloalkyl or aralkyl, $R_2$ denotes hydrogen, alkyl, cycloalkyl or aralkyl, $R_3$ denotes hydrogen or alkyl with 1 to 4 C atoms, $R_4$, if $m=1$, denotes hydrogen, alkyl, oxaalkyl, thiaalkyl, cycloalkyl, an alkylthio or alkoxy group, a substituted or unsubstituted aralkyl or aryl group or a group

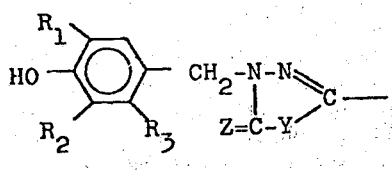

wherein $R_1$, $R_2$, $R_3$ have the above meaning and Y and Z independently of one another denote oxygen or sulphur, or, if $m=2$, denotes alkylene, oxaalkylene or thiaalkylene, vinylene or arylene, Y and Z independently of one another denote oxygen or sulphur and $m$ denotes the number 1 or 2.

Preferred compounds of the formula I are those wherein $R_1$ denotes alkyl with 1 to 8 C atoms, cycloalkyl with 6 to 8 C atoms or aralkyl with 7 to 9 C atoms, $R_2$ denotes hydrogen, alkyl with 1 to 8 C atoms, cycloalkyl with 6 to 8 C atoms or aralkyl with 7 to 9 C atoms, $R_3$ denotes hydrogen or methyl, $R_4$, if $m=1$, denotes hydrogen, alkyl with 1 to 18 C atoms, oxaalkyl or thiaalkyl with 2 to 20 C atoms, cyclohexyl, an alkylthio or alkyloxy radical with 1-18 carbon atoms, an aralkyl radical which is unsubstituted or substituted by alkyl with 1 to 4 C atoms and/or hydroxyl, a phenyl radical which is unsubstituted or substituted by halogen, hydroxyl, alkyl with 1 to 12 C atoms, alkoxy with 1 to 12 C atoms, acyloxy or acylamino groups with 2 to 18 C atoms each or alkoxycarbonyl groups with 2 to 5 C atoms, a naphthyl radical or a group

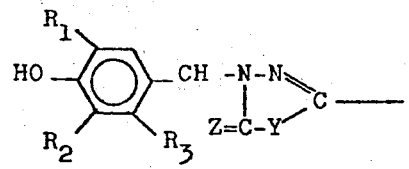

wherein $R_1$, $R_2$ and $R_3$ have the above meaning and Y and Z independently of one another denote oxygen or sulphur, or, if $m=2$, denotes alkylene with 1 to 8 C atoms, oxaalkylene or thiaalkylene with 2 to 4 C atoms, or arylene, Y and Z independently of one another denote oxygen or sulphur, and $m$ denotes the number 1 or 2.

Particularly preferred compounds of the formula I are those wherein $R_1$ and $R_2$ independently of one another denote alkyl with 1 to 5 C atoms, especially isopropyl or tert. butyl, or cycloalkyl with 6 to 8 C atoms, $R_3$ denotes hydrogen, $R_4$, if $m=1$, denotes alkyl with 1 to 18 C atoms, thiaalkyl with 2 to 14 C atoms, a hydroxyaralkyl radical which is substituted by 2 alkyl groups with 1 to 4 C atoms, a phenyl radical which is unsubstituted or substituted by a chlorine atom, a hydroxyl group, an alkyl group with 1 to 4 C atoms or an alkoxycarbonyl group with 2 to 3 C atoms, or a radical

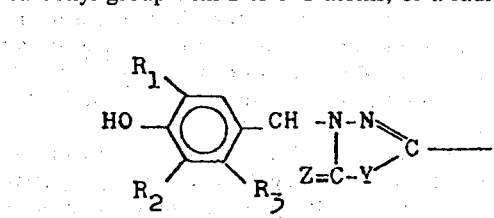

in which $R_1$, $R_2$ and $R_3$ have the above meaning and Y and Z independently of one another denote oxygen or sulphur, or, if $m = 2$, denotes alkylene with 2 to 4 C atoms, thiaalkylene with 2 to 4 C atoms or phenylene, Y and Z independently of one another denote oxygen or sulphur and m denotes the number 1 or 2.

If, in the formula I, the symbols $R_1$ or $R_2$ denote an alkyl radical, then this can be a straight-chain or branched-chain alkyl radical, such as, for example, a methyl, isopropyl, n-butyl, 2-ethylbutyl or n-octyl radical. Preferred alkyl radicals are those with 1 to 8 C atoms and the tertiary butyl radical is particularly preferred. If $R_1$ or $R_2$ denote a cycloalkyl radical, this can be, for example, a cyclohexyl, methylcyclohexyl, dimethylcyclohexyl or cyclooctyl radical. In the case of aralkyl radicals, $R_1$ or $R_2$ can be, for example, benzyl, α-methylbenzyl or α,α-dimethylbenzyl radicals.

If $R_3$ denotes alkyl with 1 to 4 C atoms, it can be, for example, ethyl, isopropyl or tert.butyl. Preferably, $R_3$ represents a methyl group.

If R₄ in the formula I denotes an alkyl radical, then this can be a straight-chain or branched-chain or branched-chain alkyl radical, for example a methyl, ethyl, n-propyl, isopropyl, n-butyl, ethylhexyl, isodecyl, octadecyl or trimethylhexyl radical.

If R₄ denotes an oxaalkyl or thiaalkyl radical, then these are radicals of the formula $C_xH_{2x+1}$—Q—$C_yH_{2y}$—, wherein Q represents an oxygen or sulphur atom and x and y are integers of which the sum is preferably 2 to 20. Examples thereof are the radicals: $C_2H_5$—O—$CH_2CH_2$—, $C_2H_5$—O—$CH_2CH_2CH_2$—, $C_6H_{13}$—O—$CH_2$—, $C_4H_9$—S—$CH_2CH_2$—, $C_{12}H_{25}$—S—$CH_2CH_2$— and $C_{18}H_{37}$—S—$CH_2$—.

If R₄ denotes a cycloalkyl radical, this can be, for example, a cyclooctyl, a cyclohexyl or a methylcyclohexyl radical. It is preferably a cyclohexyl radical.

If R₄ denotes an alkylthio or alkoxy group, this can be, for example, a butylthio, dodecylthio, tert.butylthio, methoxy, propyloxy, hexyloxy, tetradecyloxy or octadecyloxy group.

Aralkyl radicals represented by R₄ can be unsubstituted or substituted. Possible substituted aralkyl radicals are above all radicals substituted by alkyl groups with 1 to 4 C atoms each, and/or by a hydroxyl group. Thus, for example, such radicals can be a benzyl, phenylethyl, phenylpropyl, diphenylmethyl, tolylmethyl, α,α-dimethylbenzyl, 3-hydroxybenzyl, 3-methyl-4-hydroxybenzyl or 2-(3-tert.butyl-4-hydroxyphenyl)-ethyl radical. They are preferably an aralkyl radical which is substituted by two alkyl groups with 1 to 4 C atoms and one hydroxyl group, such as, for example, the 3,5-di-tert.butyl-4-hydroxybenzyl, 2-(3,5-dimethyl-4-hydroxyphenyl)-ethyl or 2-(3,5-di-tert.butyl-4-hydroxyphenyl)-ethyl radical.

When R₄ denotes an aryl radical, it is in particular an unsubstituted phenyl or naphthyl radical or a substituted phenyl radical. Possible substituents of such phenyl radicals are above all halogen atoms, such as bromine, fluorine, iodine and especially chlorine, hydroxyl, alkyl with up to 12 C atoms, especially those with 1 to 4 C atoms, alkoxy with 1 to 18 C atoms, acylamino or acyloxy groups with 2 to 18 C atoms each or alkoxycarbonyl groups with 2 to 5 C atoms. In general, phenyl radicals represented by R₄ do not possess more than two of the abovementioned substituents. As examples of such substituted phenyl radicals there may be mentioned: chlorophenyl, dichlorophenyl, bromophenyl, hydroxyphenyl, methylphenyl, dimethylphenyl, ethylphenyl, isobutylphenyl, n-butylphenyl, di-t-butylphenyl, methoxyphenyl, dimethoxyphenyl, ethoxyphenyl, di-n-butoxyphenyl, iso-octyloxyphenyl, dodecyloxyphenyl, octadecyloxyphenyl, acetylaminophenyl, n-butyrylaminophenyl, lauroylaminophenyl, acetoxyphenyl, mono- and di-n-propionyloxyphenyl, octanoyloxyphenyl, mono-, and distearoyloxyphenyl, methoxy-, ethoxy- and n-butoxycarbonylphenyl.

Particularly preferred aryl radicals R₄ are the unsubstituted phenyl radical or a phenyl radical substituted by a chlorine atom, a hydroxyl group, an alkyl group with 1 to 4 C atoms or an alkoxycarbonyl group with 2 or 3 C atoms.

If R₄ in the formula I denotes a group

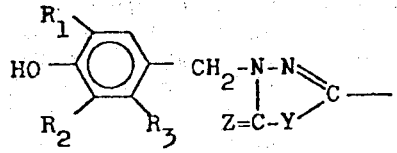

R₁, R₂, R₃, Y and Z have the same meaning as in the remainder of the molecule, so that such compounds are symmetrical bisoxadiazolyl or bis-thiadiazolyl derivatives of the formula

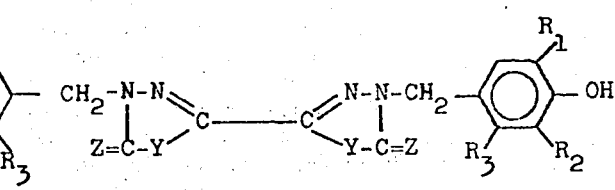

wherein the symbols have the initially mentioned meaning.

If R₄ in the formula I (in the case that m=2) denotes an alkylene radical, this can be a straight-chain or branched radical. Examples thereof are the radicals: —$CH_2$—, —$CH_2CH_2$—, —$(CH_2)_4$—, —$(CH_2)_8$—,

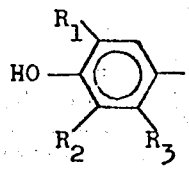

and

If R₄ denotes an oxaalkylene or thiaalkylene radical, these can be radicals of the formula —$C_xH_{2x}$—Q—$C_yH_{2y}$—, wherein Q denotes an oxygen or sulphur atom and x and y are integers of which the sum is preferably 2 to 4. Examples thereof are the radicals —$CH_2$—O—$CH_2$—, —$CH_2$—$CH_2$—S—$CH_2$—$CH_2$— or —$CH_2$—S—$CH_2$—.

If R₄ denotes an arylene radical, this can be, for example, a phenylene, diphenylene or naphthylene radical. Preferably it is phenylene.

Examples of compounds according to the invention, of the formula I: 3-(3,5-di-tert.butyl-4-hydroxybenzyl)-5-phenyl-1,3,4-oxadiazol-2-one, 3-(3,5-di-tert.butyl-4-hydroxybenzyl)-5-p-tolyl-1,3,4-oxadiazole-2-thione, 3-(3,5-di-tert.butyl-4-hydroxybenzyl)-5-(4-hydroxybenzyl)-1,3,4-oxadiazol-2-one, 3-(3,5-dimethyl-4-hydroxybenzyl)-5-(2-hydroxyphenyl)-1,3,4-oxadiazol-2-one, 3-(3-methyl-4-hydroxy-5-tert. butylbenzyl)-5-(4-methoxyphenyl)-1,3,4-oxadiazole-2-thione, 3-(3-tert.butyl-4-hydroxybenzyl)-5-(4-chlorophenyl)-1,3,4-thiadiazole-2-thione, 3-(3-tert.butyl-4-hydroxy-6-methyl)-5-(3-stearoyloxyphenyl)-1,3,4-oxadiazol-2-one, 3-(3,5-di-tert.octyl-4-hydroxybenzyl)-5-dodecylmercapto-1,3,4-oxadiazole-2-thione, 3-(3,5-ditert. butyl-4-hydroxybenzyl)-5-ethoxy-1,3,4-thiadiazol-2-one, 3-(3,5-di-tert.butyl-4-hydroxybenzyl)-5-(3-thiapentadecyl)-1,3,4-oxadiazol-2-one, 3-(3-tert.butyl-4-hydroxybenzyl)-5-(2-butoxyethyl)-1,3,4-oxadiazol-2-one, 3-(3-di-tert.butyl-4-hydroxybenzyl)-5-(3-methoxycarbonylphenyl)-1,3,4-oxadiazol-2-one, 3-(3,5-di-tert.butyl-4-hydroxybenzyl)-5-(3-acetylaminophenyl)-1,3,4-oxadiazol-2-one, 3-(3,5-di-tert.butyl-4-hydroxybenzyl)-5-[2-(3,5-di-tert.butyl-4-hydroxyphenyl)-ethyl]-1,3,4-thiadiazol-2-one, di-[3-(3,5-di-tert.butyl-4-hydroxybenzyl)-2-oxo-1,3,4-oxadiazolin-5-yl],1,4-di-[3-(3,5-di-tert.butyl-4-hydroxybenzyl)-2-oxo-1,3,4-oxadiazolin-5-yl]butane, 4,4'-di-[3-(3-tert.butyl-4-hydroxybenzyl)-2-oxo-1,3,4-oxadiazolin-5-yl]-diphenyl, 1,5-di-[3-(3-tert.butyl-4-hydroxy-5-methyl)-2-oxo-1,3,4-thiadiazolin-5-yl]-3-thiapentane and 1,2-di-[3-(3,5-di-tert.butyl-4-hydroxybenzyl)-2-oxo-1,3,4-oxadiazolin-5-yl]-ethylene.

The compounds according to the invention, of the formula I, can be prepared by reacting a compound of the formula II

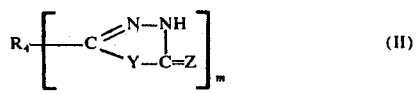

either a. simultaneously with at least $m$ mols of formaldehyde or a formaldehyde donor and with $m$ mols of a compound of the formula III

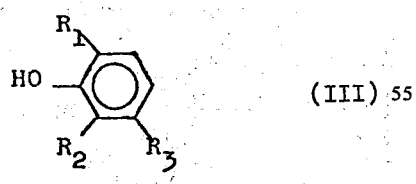

or b. stepwise, first with at least $m$ mols of formaldehyde or of a formaldehyde donor to give a compound of the formula IV

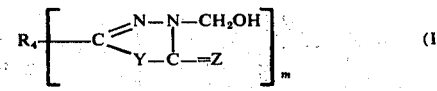

which is then reacted with $m$ mols of a compound of the formula III, the symbols $R_1$, $R_2$, $R_3$, $R_4$, Y, Z and $m$ in these formulae having the same meaning as in the formula I.

The oxadiazole and thiadiazole compounds of the formula II used as starting material are known compounds. Examples thereof are: 5-phenyl-1,3,4-oxadiazol-2-one, 5-tert. butyl-1,3,4-oxadiazol-2-one, 5-p-tolyl-1,3,4-oxadiazol-2-thione, 5-phenyl-1,3,4-thiadiazole-2-thione, 3,3'-di-(4-hydroxybenzyl)-5,5'-bis-(1,3,4-oxadiazol-2-one), 5-(dodecylmercaptoethyl)-1,3,4-oxadiazol-2-one, 5-tert.butylmercapto-1,3,4-thiadiazol-2-one, 5-methoxy-1,3,4-oxadiazol-2-one and 1,3-di-(2-oxo-1,3,4-oxadiazolin-5-yl)-benzene.

The alkylphenols of the formula III used as starting material are also known compounds. As examples there may be mentioned: 2,6-di-tert.butylphenol, 2-t-butyl-6-methylphenol, 2,6-di-tert.butyl-3-methylphenol, 2,5-dimethylphenol and 2,6-dioctylphenol.

The simultaneous reaction of these two starting components with formaldehyde or a formaldehyde donor according to (a) is advantageously carried out in a polar solvent, such as dimethylformamide, dimethylacetamide, methanol or ethanol or their mixtures with water. The formaldehyde donor used can be an oligomer or polymer of formaldehyde, preferably paraformaldehyde. The addition of a basic catalyst, especially of hexamethylenetetramine, can be of advantage.

The reaction takes place in the sense of Equation 1

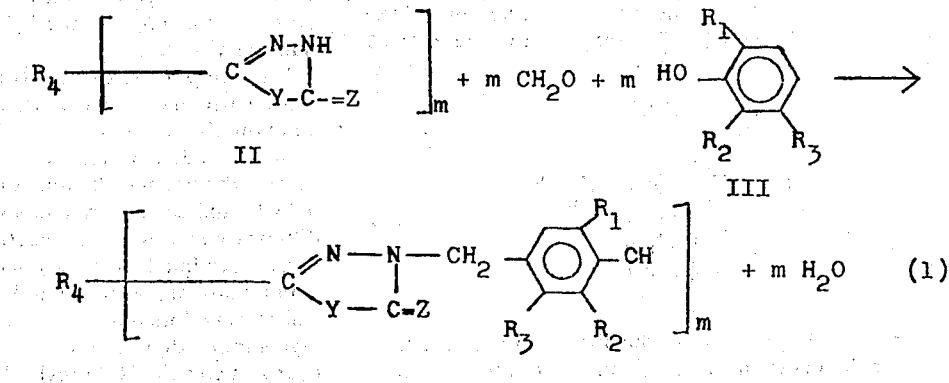

Hence, one mol of II requires $m$ mols of III and $m$ mols of formaldehyde. However, because of the volatility of formaldehyde it is advisable to use the latter in excess. The reaction is usually carried out at an elevated temperature, suitably at about 80–130°C. It gives the compounds according to the invention, of the formula I, direct, with elimination of $m$ mols of water.

In the stepwise reaction according to (b), the compounds of the formula II are first reacted in accordance with Equation 2 with $m$ mols of formaldehyde or a formaldehyde donor and the 3-hydroxymethyl-oxadiazoline or 3-hydroxymethyl-thiadiazoline derivatives of the formula IV, thus obtained, are reacted in a second reaction stage, in accordance with Equation 3, with $m$ mols of a compound of the formula III.

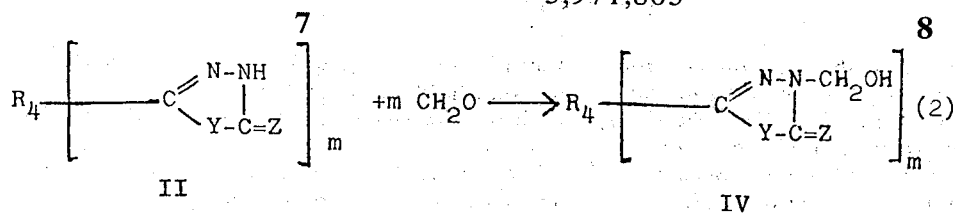

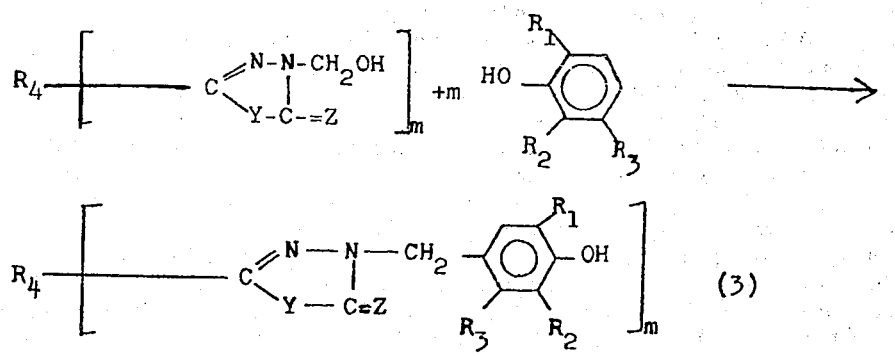

The reaction according to Equation 2 is also suitably carried out with a slight excess of formaldehyde. Suitable reaction media are water or polar solvents or their mixtures with water.

As the formaldehyde donor, paraformaldehyde can above all be used. The methylol compounds of the formula IV can be isolated but they can also immediately be reacted further with the phenols of the formula III in accordance with Equation 3. This second stage reaction can be catalysed with bases such as hexamethylenetetramine.

A modification of the process of manufacture from components II, III and formaldehyde, which has been described, consists of reacting the compounds of the formula II with one mol of a compound of the formula V

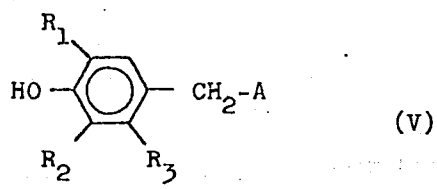

wherein $R_1$, $R_2$ and $R_3$ have the abovementioned meaning and A denotes a halogen atom, preferably chlorine, or a group $$-N\begin{matrix}R_5\\R_5\end{matrix}$$

or a group $$-S-\overset{\overset{S}{\|}}{C}-N\begin{matrix}R_5\\R_5\end{matrix}$$

wherein $R_5$ represents an alkyl radical with 1 to 4 C atoms, for example a methyl, ethyl, isopropyl or tertiary butyl radical.

The compounds of the formula V are known substances which can be manufactured, for example, from compounds of the formula III by chloromethylation with formaldehyde and hydrochloric acid or - in the case of the amines - by aminomethylation with formaldehyde and secondary amines or - in the case of the dithiocarbamates - by reaction with formaldehyde, carbon disulphide and a secondary amine. Examples of compounds of the formula V are: 2,6-di-tert.butyl-4-chloromethylphenol, 2,6-di-tert.butyl-4-(N,N-dimethylaminomethyl)phenol or 3,5-di-tert.butyl-4-hydroxybenzyl-N,N-diethyldithiocarbamate.

This reaction takes place in the sense of equation 4:

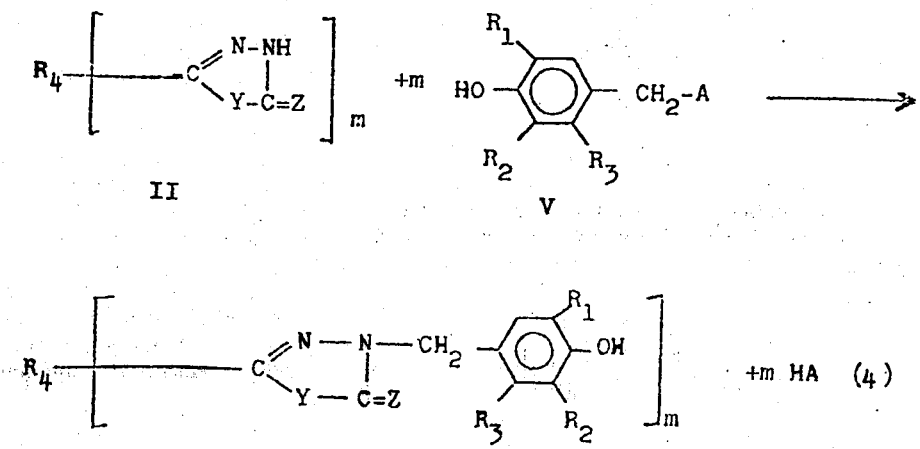

If A denotes a halogen atom, m mols of hydrogen halide are produced and it is advisable to add stoichiometric amounts of a base, such as triethylamine or pyridine, to neutralise it. The reaction in that case is preferably carried out in a polar solvent such as dimethylformamide, dimethylacetamide or a lower alcohol.

If A denotes a group

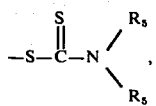

it is again advisable to use a polar solvent or its mixture with water. In this case, again, the reaction is advantageously carried out with addition of stoichiometric amounts of a base. As such, it is possible to use an inorganic base such as an alkali metal hydroxide or alkali metal carbonate, or an organic base such as a trialkylamine or a heterocyclic base.

If A denotes a group

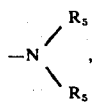

the reaction is advantageously carried out in an anhydrous solvent, for example in benzene, toluene, dioxane, dimethylformamide or dimethylacetamide, and with addition of catalytic amounts of a base, for example of lithium amide, sodium amide, calcium hydride, sodium hydroxide, potassium hydroxide or sodium methylate.

In all cases of the reaction with compounds of the fomula V, elevated temperatures, preferably 50°–150°C, are used. In cases where bases are added it can be appropriate to neutralise these, before working up, with an acid such as acetic acid or hydrochloric acid.

In all the process variants described, the end products can be isolated in accordance with the customary methods, for example by distilling off a part of the solvent or by diluting with water and filtering off the products which have precipitated. The end products of the formula I are crystalline substances and can therefore be purified by recrystallisation.

According to the present invention, the compounds of the formula I can be used as stabilisers for organic substrates. Examples of possible substrates are:

1. Polymers which are derived from hydrocarbons with single or double unsaturation, such as polyolefines, for example polyethylene, which can optionally be crosslinked, polypropylene, polyisobutylene, polymethylbutene-1, polymethylpentene-1, polybutene-1, polyisoprene, polybutadiene, polystyrene, copolymers of the monomers on which the homopolymers mentioned are based, such as ethylenepropylene copolymers, propylene-butene-1 copolymers, propylene-isobutylene copolymers, styrene-butadiene copolymers and terpolymers of ethylene and propylene with a diene, such as, for example, hexadiene, dicyclopentadiene or ethylidenenorbornene; mixtures of the abovementioned homopolymers, such as, for example, mixtures of polypropylene and polyethylene, polypropylene and polybutene-1, or polypropylene and polyisobutylene.

2. Vinyl polymers containing halogen, such as polyvinyl chloride, polyvinylidene chloride, polyvinyl fluoride, but also polychloroprene and chlorinated rubbers.

3. Polymers which are derived from $\alpha,\beta$-unsaturated acids and their derivatives, such as polyacrylates and polymethacrylates, polyacrylamides and polyacrylonitrile, as well as their copolymers with other vinyl compounds, such as acrylonitrile/butadiene/styrene, acrylonitrile/styrene and acrylonitrile/styrene/acrylic ester copolymers.

4. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl-butyral, polyallyl phthalate, polyallyl-melamine and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers.

6. Polyacetals, such as polyoxymethylene and polyoxyethylene, as well as those polyoxymethylenes which contain ethylene oxide as the comonomer.

7. Polyphenylene oxides.
8. Polyurethanes and polyureas.
9. Polycarbonates.
10. Polysulphones.
11. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.
12. Polyesters which are derived from dicarboxylic acids and dialcohols and/or from hydroxycarboxylic acids or the corresponding lactones, such as polyethylene glycol terephthalate or poly-1,4-dimethylolcyclohexane terephthalate.
13. Crosslinked polymers which are derived from aldehydes on the one hand and phenols, ureas and melamines on the other, such as phenol-formaldehyde, urea-formaldehyde and melamine-formaldehyde resins.
14. Alkyd resins, such as glycerine-phthalic acid resins and their mixtures with melamine-formaldehyde resins.
15. Unsaturated polyester resins which are derived from copolyesters of saturated and unsaturated dicarboxylic acids with polyhydric alcohols, with vinyl compounds as crosslinking agents, and also their halogen-containing modifications of low inflammability.
16. Natural polymers such as cellulose, rubber, proteins and their polymer-homologously chemically modified derivatives, such as cellulose acetates, cellulose propionates and cellulose butyrates, or the cellulose ethers, such as methylcellulose.
17. High molecular monomeric substances, for example mineral oils, animal and vegetable fats, oils and waxes, or oils, waxes and fats based on synthetic esters.

The use of the compounds of the formula I for stabilising homopolymers and copolymers of olefines, such as the substrates mentioned under 1., and stabilising polyamides and polyurethanes, is of particular importance.

The compounds of the formula I are in general incorporated into the substrates in a concentration of 0.01 to 5% by weight calculated relative to the material to be stabilised. Preferably 0.05 to 2.0, and particularly preferentially 0.1 to 1.0, % by weight of the compounds, calculated relative to the material to be stabilised, are incorporated into the latter. The incorporation can take place, for example, by mixing in at least one of the compounds of the formula I and optionally further additives according to the methods customary in the art, before or during shaping, or by applying the dissolved or dispersed compounds to the polymer, if appropriate with subsequent evaporation of the solvent.

In the case of crosslinked polyethylene the compounds of the formula I are suitably added before crosslinking. The compounds of the formula I can also be added before or during the polymerisation.

As further additives together with which the stabilisers according to the invention can be employed there should be mentioned:

1. Antioxidants 1.1. Simple 2,6-dialkylphenols, such as, for example, 2,6-di-tert.-butyl-4-methylphenol, 2-tert.-butyl-4,6-dimethylphenol, 2,6-di-tert.-butyl-4-methoxy-methylphenol and 2,6-dioctadecyl-4-methylphenol.

1.2. Derivatives of alkylated hydroquinones, such as, for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxy-anisole, tris-(3,5-di-tert.-butyl-4-hydroxyphenyl) phosphite, 3,5-di-tert.-butyl-4-hydroxyphenyl stearate and bis-(3,5-di-tert.-butyl-4-hydroxyphenyl) adipate.

1.3. Hydroxylated diphenyl thioethers, such as, for example, 2,2'-thio-bis-(6-tert.-butyl-4-methylphenol), 2,2'-thio-bis-(4-octylphenol), 4,4'-thiobis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl)-disulphide.

1.4. Alkylidene-bisphenols, such as for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butylphenol), 2,6-di-(3-tert.-butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl) pentane and ethylene glycol bis-[3,3-bis-(3'-tert.-butyl-4'-hydroxyphenyl)-butyrate].

1.5. O-, N- and S-benzyl compounds, such as, for example, 3,5,3',5'-tetra-tert.-butyl-4,4'-dihyroxybenzyl ether, 4-hydroxy-3,5-dimethylbenzyl-mercaptoacetic acid octadecyl ester, tris-(3,5-di-tert.-butyl-4-hydroxybenzyl)-amine and bis-(4-tert.-butyl-3-hydroxy-2,6-dimethylbenzyl) dithioterephthalate. 1.6. Hydroxybenzylated malonic esters, such as, for example, 2,2-bis-(3,5-di-tert.-butyl-2-hydroxybenzyl)-malonic acid dioctadecyl ester, 2-(3-tert.-butyl-4-hydroxy-5-methylbenzyl)malonic acid dioctadecyl ester, 2,2-bis-(3,5-di-tert.-butyl-4-hydroxybenzyl)-malonic acid didodecylmercapto-ethyl ester and 2,2-bis-(3,5-di-tert.-butyl-4-hydroxybenzyl)-malonic acid di[4-(1,1,3,3-tetramethylbutyl)-phenyl] ester. 1.7. Hydroxybenzyl-aromatic compounds, such as, for example, 1,3,5-tri-(3,5-di-tert.-butyl-4-hydroxybenzyl)-2,4,6-trimethylbenzene, 1,4-di-(3,5-di-tert.-butyl-4-hydroxybenzyl)-2,3,5,6-tetramethylbenzene and 2,4,6-tri-(3,5-di-tert.-butyl-4-hydroxybenzyl)-phenol.

1.8. s-Triazine compounds, such as, for example, 2,4-bisoctylmercapto-6-(3,5-di-tert.-butyl-4-hydroxyanilino)-s-triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl) isocyanurate.

1.9. Amides of β-(3,5-di-tert.-butyl-4-hydroxyphenyl) propionic acid, such as, for example, 1,3,5-tris-(3,5-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine.

1.10. Esters of β-(3,5-di-tert.-butyl-4-hydroxyphenyl)propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]-octane.

1.11. Esters of β-(5-tert.-butyl-4-hydroxy-3-methylphenyl)propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]-octane.

1.12. Esters of 3,5-di-tert.-butyl-4-hydroxyphenylacetic acid with monohydric or polyhydric alcohols such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]octane.

1.13. Acylaminophenols, such as, for example, N-(3,5-di-tert.-butyl-4-hydroxyphenyl)-stearic acid amide and N,N'-di-(3,5-di-tert.-butyl-4-hydroxyphenyl)-thio-bis-acetamide.

1.14. Benzylphosphonates, such as, for example, 3,5-di-tert.-butyl-4-hydroxybenzyl-phosphonic acid dimethyl ester, 3,5-di-tert.-butyl-4-hydroxybenzyl-phosphonic acid diethyl ester, 3,5-di-tert.-butyl-4-hydroxybenzyl-phosphonic acid dioctadecyl ester and 5-tert.-butyl-4-hydroxy-3-methylbenzyl-phosphonic acid dioctadecyl ester.

1.15. Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-di-sec.-butyl-p-phenylenediamine, 6-ethoxy-2,2,4-trimethyl-1,2-dihydroquinoline, 6-dodecyl-2,2,4-trimethyl-1,2-dihydroquinoline, mono- and di-octyliminodibenzyl, polymerised 2,2,4-trimethyl-1,2-dihydroquinoline, octylated diphenylamine, nonylated diphenylamine, N-phenyl-N'-cyclohexyl-p-phenylenediamine, N-phenyl-N'-isopropyl-p-phenylenediamine, N,N'-di-sec.-octyl-p-phenylenediamine, N-phenyl-N'-sec.-octyl-p-phenylenediamine, N,N'-di-(1,4-dimethylpentyl)-p-phenylenediamine, N,N'-dimethyl-N,N'-di-(sec.-octyl)-p-phenylenediamine, 2,6-dimethyl-4-methoxyaniline, 4-ethoxy-N-sec.-butylaniline, diphenylamine-acetone condensation product, aldol-1-naphthylamine and phenothiazine.

2. UV-absorbers and light protection agents 2.1. 2-(2'-Hydroxyphenyl)-benztriazoles, such as, for example, the 5'-methyl-, 3',5'-di-tert.-butyl-, 5'-tert.-butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 3'-α-methylbenzyl-5'-methyl, 3'-α-methylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl- and 5-chloro-3',5'-di-tert.-amyl-derivative.

2.2. 2,4-bis-(2'-Hydroxyphenyl)-6-alkyl-s-triazines, such as, for example, the 6-ethyl-, 6-heptadecyl- and 6-undecyl-derivative.

2.3 2-Hydroxybenzophenones, such as, for example, the 4-hydroxy-, 4-methoxy, 4-octoxy-, 4-decyloxy-, 4-dodecyloxy-, 4-benzyloxy-, 4,2',4'-trihydroxy- and 2'-hydroxy-4,4'-dimethoxy derivative.

2.4 1,3-bis-(2'-Hydroxybenzoyl)-benzenes, such as, for example, 1,3-bis-(2'-hydroxy-4'-hexyloxy-benzoyl)-benzene, 1,3-bis-(2'-hydroxy-4'-octyloxy-benzoyl)-benzene and 1,3-bis-(2'-hydroxy-4'-dodecyloxy-benzoyl)-benzene.

2.5 Esters of optionally substituted benzoic acids, such as, for example, phenyl salicylate, octylphenyl salicylate, dibenzoylresorcinol, bis-(4-tert.-butylbenzoyl)-resorcinol, benzoylresorcinol, 3,5-di-tert.-butyl-4-hydroxybenzoic acid 2,4-di-tert.-butylphenyl ester or octadecyl ester or 2-methyl-4,6-di-tert.-butylphenyl ester.

2.6. Acrylates, such as, for example, α-cyano-β,β-diphenylacrylic acid ethyl ester and isooctyl ester, α-carbomethoxycinnamic acid methyl ester, α-cyano-β-methyl-p-methoxy-cinnamic acid methyl ester and butyl ester and N-(β-carbomethoxyvinyl) 2-methylindoline.

2.7 Nickel compounds, such as, for example, nickel complexes of 2,2'-thio-bis [4-(1,1,3,3-tetramethylbutyl)-phenol], such as the 1:1- or the 1:2-complex, optionally with additional ligands such as n-butylamine, triethanolamine or N-cyclohexyl-diethanolamine, nickel complexes of bis-[2-hydroxy-4-(1,1,3,3-tetramethylbutyl)-phenyl]-sulphone, such as the 2:1-complex, optionally with additional ligands such as 2-ethylcaproic acid, nickel dibutyldithiocarbamate, nickel salts of 4-hydroxy-3,5-di-tert.- butylbenzyl-phosphonic acid monoalkyl esters, such as of the methyl, ethyl or butyl ester, nickel complexes of ketoximes such as of 2-hydroxy-4-methylphenyl-undecylketonoxime, nickel 3,5-di-tert.-butyl-4-hydroxybenzoate and nickel isopropylxanthate.

2.8. Sterically hindered amines, such as, for example, 4-benzoyloxy-2,2,6,6-tetramethylpiperidine, 4-stearoyloxy-2,2,6,6-tetramethylpiperidine, bis-(2,2,6,6-tetramethylpiperidyl) sebacate and 3-n-octyl-7,7,9,9-tetramethyl-1,3,8-triaza-spiro [4,5]decane-2,4-dione.

2.9. Oxalic acid diamides, such as, for example, 4,4'-di-octyloxy-oxanilide, 2,2'-di-octyloxy-5,5'-di-tert.-butyl-oxanilide, 2,2'-di-dodecyloxy-5,5'-di-tert.-butyloxanilide, 2-ethoxy-2'-ethyl-oxanilide, N,N'-bis-(3-dimethylaminopropyl) oxalamide, 2-ethoxy-5-tert.-butyl-2'-ethyl-oxanilide and its mixture with 2-ethoxy-2'-ethyl-5,4'-di-tert.-butyl-oxanilide and mixtures of ortho- and para-methoxy-disubstituted and o- and p-ethoxy-disubstituted oxanilides.

3. Metal deactivators, such as, for example, oxanilide, isophthalic acid dihydrazide, sebacic acid bis-phenylhydrazide, bis-benzylidene oxalic acid dihydrazide, N,N'-diacetyl-adipic acid dihydrazide, N,N'-bis-salicyloyl-oxalic acid dihydrazide, N,N'-bis-salicyloylhydrazine, N,N'-bis-(3,5-di-tert.-butyl-4-hydroxyphenylpropionyl)-hydrazine, N-salicylal-N'-salicylidene hydrazine and 3-salicyloylamino-1,2,4-triazole.

4. Phosphites, such as, for example, triphenyl phosphite, diphenyl alkyl phosphites, phenyl dialkyl phosphites, tri (nonylphenyl) phosphite, trilauryl phosphite, trioctadecyl phosphite, 3,9-di-isodecyloxy-2,4,8,10-tetroxa-3,9-diphospha spiro [5,5]undecane and tri-(4-hydroxy-3,5-di-tert.-butylphenyl) phosphite.

5. Compounds which destroy peroxide, such as, for example, esters of β-thio-dipropionic acid, for example the lauryl, stearyl, myristyl or tridecyl ester, mercaptobenzimidazole and the zinc salt of 2-mercaptobenzimidazole.

6. Polyamide stabilisers, such as, for example, copper salts in combination with iodides and/or phosphorus compounds and salts of divalent manganese.

7. Basic co-stabilisers, such as, for example, melamine, benzoguanamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example Ca stearate, Zn stearate, Mg stearate, Na ricinoleate and K palmitate, antimony pyrocatecholate or tin pyrocatecholate.

8. PVC stabilisers, such as, for example, organic tin compounds, organic lead compounds and barium -cadmium salts of fatty acids.

9. Nucleating agents, such as, for example, 4-tert.-butyl-benzoic acid, adipic acid and diphenylacetic acid.

10. Urea derivatives, such as, for example, N-cyclohexyl-N'-1-naphthylurea, N-phenyl-N,N'-dicylcohexylurea, N-phenyl-N'-2-naphthylurea, N-phenylthiourea and N,N'-dibutylthiourea.

11. Other additives, such as, for example, plasticisers, lubricants, emulsifiers, fillers, carbon black, asbestos, kaolin, talc, glass fibres, pigments, optical brighteners, flameproofing agents and antistatic agents.

The invention is explained in more detail in the examples which follow. In these, percentages (%) denote percentages by weight and parts denote parts by weight.

EXAMPLE 1

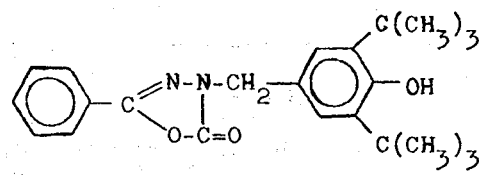

a. 32.4 g of 5-phenyl-1,3,4-oxadiazol-2-one (0.2mol) are suspended in 200 ml of water, the mixture is brought to pH 10 with sodium carbonate and 27 ml of aqueous approx. 33% strength formaldehyde solution (approx. 0.3 mol) are added. The reaction mixture is stirred for 10 hours at room temperature (approx. 20°–25°C), producing a homogeneous, fine suspension. The resulting 5-phenyl-3-hydroxymethyl-1,3,4-oxadiazol-2-one is filtered off, well washed with water and dried in vacuo at 30°C.

It melts at 150°C, with elimination of formaldehyde.

b. 19.2 g of 5-phenyl-3-hydroxymethyl-1,3,4-oxadiazol-2-one (0.1 mol), 20.6 g of 2,6-di-tert.-butyl-phenol (0.1 mol) and 0.4 g of hexamethylenetetramine in 100 ml of dimethylformamide and 10 ml of water are heated for 16 hours to 110°C, whilst stirring. After cooling the reaction mixture to about 25°C, 3-(3,5-di-tert.-butyl-4-hydroxy-benzyl-5-phenyl-1,3,4-oxadiazol-2-one (stabiliser No. 1) crystallises out. The crystals are filtered off, washed with methanol and dried.

Melting point: 164°C.

EXAMPLES 2–6

40.5 g of 5-phenyl-1,3,4-oxadiazol-2-one (0.25 mol), 51.5 g of 2,6-di-tert.-butyl-phenol (0.25 mol), 8.2 g of paraformaldehyde (0.27 mol) and 0.7 g of hexamethylenetetramine in 150 ml of dimethylformamide and 15 ml of water are heated to 110°C for 15 hours, whilst stirring. A yellowish solution results, from which the 3-(3,5-di-tert.-butyl-4-hydroxybenzyl)-5-phenyl-1,3,4-oxadiazol-2-one (stabiliser No. 1) which is formed crystallises out on cooling to room temperature. The product is filtered off, washed with a little methanol and dried in vacuo at 70°C. Melting point: 164°C.

If, in the above example, 5-phenyl-1,3,4-oxadiazol-2-one is replaced by an equivalent amount of one of the 5-phenyl-1,3,4-oxadiazol-2-ones, substituted in the benzene nucleus, which are shown in Table 1 which follows, the corresponding 3,5-di-tert.-butyl-4-hydroxybenzyl derivatives, having the melting points listed, are obtained.

TABLE 1

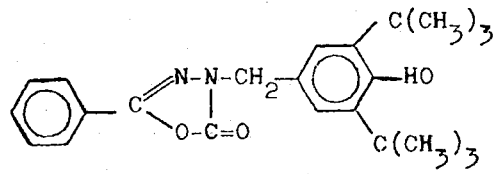

| R | Melting Point | Stabiliser |
|---|---|---|
| CH₃—⟨◯⟩— | 153°C | 2 |
| (CH₃)₃C—⟨◯⟩— | 176°C | 3 |
| Cl—⟨◯⟩— | 141°C | 4 |
| ⟨◯⟩—OH | 174°C | 5 |

EXAMPLE 7

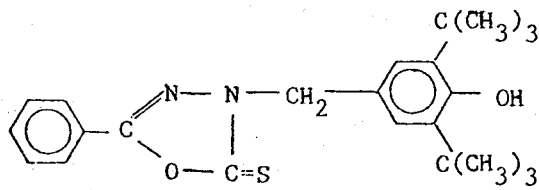

40.5 g of 5-phenyl-1,3,4-oxadiazol-2-one (0.25 mol) and 92 g of N,N-diethyl-dithiocarbamic acid (3,5-di-tert.-butyl-4-hydroxybenzyl) ester (0.25 mol) are dissolved in 750 ml of ethanol at 60°C. After dropwise addition of 10 g of sodium hydroxide in 50 ml of water, the mixture is stirred for 7 hours at 60°C. On cooling, 3-(3,5-di-tert.-butyl-4-hydoxybenzyl)-5-phenyl-1,3,4-oxadiazol-2-one (stabiliser No. 1) crystallises out. The product is filtered off, washed with a little methanol and dried in vacuo at 70°C. Melting point: 164°C.

EXAMPLES 8 and 9

35.6 g of 5-phenyl-1,3,4-oxadiazole-2-thione (0.2 mol), 41.2 g of 2,6-di-tert.-butylphenol (0.2 mol), 6,6 g of paraformaldehyde (0.22mol) and 0.5 g of hexamethylenetetramine in 130 ml of dimethylformamide and 13 ml of water are heated to 110°C for 7 hours, whilst stirring. After cooling, the reaction mixture is stirred into 500 ml of ice water and the product which precipitates is isolated. For purification, the reaction product is repeatedly digested with methanol, filtered off and dried. 3-(3,5-di-t-Butyl-4-hydroxybenzyl)-5-phenyl-1,3,4-oxadiazole-2-thione (stabiliser N0. 6), thus obtained, has a melting point of 166°C.

If, in the preceding example, 5-phenyl-1,3,4-oxadiazole-2-thione is replaced by an equivalent amount of 5-(p-tolyl)-1,3,4-oxadiazole-2-thione and otherwise the same procedure is followed, 3-(3,5-di-t.-butyl-4-hydroxybenzyl-5-(p-tolyl)-1,3,4-oxadiazole-2-thione (stabiliser No. 7) of melting point 159°C is obtained.

EXAMPLES 10 and 11

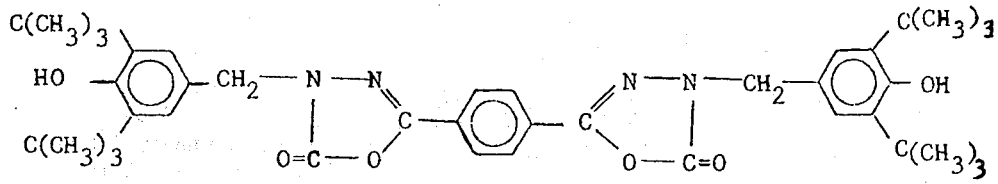

24.6 g of 1,4-di-(2-oxo-1,3,4-oxadiazolin-5-yl)-benzene (0.1 mol), 41.2 g of 2,6-di-tert.-butylphenol (0.2 mol), 6.6 g of paraformaldehyde (0.22 mol) and 0.5 g of hexamethylenetetramine in 130 ml of dimethylformamide and 13 ml of water are heated for 3 hours to 110°C, whilst stirring. A colourless solution is first produced, from which the reaction product precipitates. After cooling, the product is isolated, thoroughly washed with methanol and dried.

The 1,4-di[2-oxo-3(3,5-di-tert.-butyl-4-hydroxybenzyl)-1,3,4-oxadiazolin-5-yl]-benzene (stabiliser No. 8) which is obtained melts at 281°C.

If in this example 1,4-bis-(2-oxo-1,3,4-oxadiazlin-5-yl)benzene is replaced by equivalent amount of 1,3-bis(2-oxo-1,3,4-oxadiazolin-5-yl)-benzene and otherwise the same procedure is followed, 1,3,-bis-[2-oxo-3-(3,4-di-tert.-butyl-4-hydroxybenzyl)-1,3,4-oxadiazolin-5-yl]-benzene (stabiliser No. 9) of melting point 220°C is obtained.

EXAMPLE 12

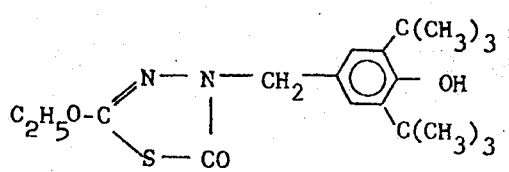

29.2 g of 5-ethoxy-1,3,4-thiadiazol-2-one (0.2 mol) and 53.0 g of N,N-dimethyl-3,5-di-t.-butyl-4-hydroxybenzylamine (0.2 mol) are dissolved in 200 ml of dimethylformamide at 80°C and the solution is kept at this temperature for 15 hours. At the same time the dimethylamine formed is expelled from the reaction solution by means of a gentle stream of nitrogen. The mixture is then poured onto about 500 ml of ice water, whereupon the reaction product initially precipitates in an amorphous form and soon solidifies to crystals. The filter residue is purified by washing with a little cold methanol and is dried at 60°C. The resulting 3-(3,5-di-t.-butyl-4-hydroxybenzyl)-5-ethoxy-1,3,4-thiadiazol-2-one forms colourless crystals and melts at 119°C.

EXAMPLE 13

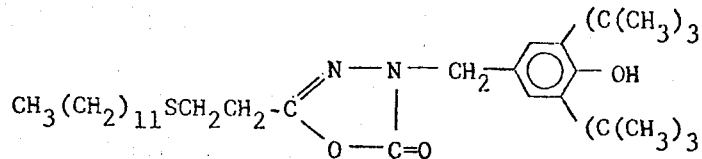

If, in Example 12, 5-ethoxy-1,3,4-thiadiazol-2-one is replaced by the equivalent amount of 5-dodecylmercaptoethyl-1,3,4-oxadiazol-2-one and otherwise the same procedure is followed, 3-(3,5-di-t.-butyl-4-hydroxybenzyl)-5-dodecylmercaptoethyl-1,3,4-oxadiazol-2-one is obtained.

EXAMPLE 14

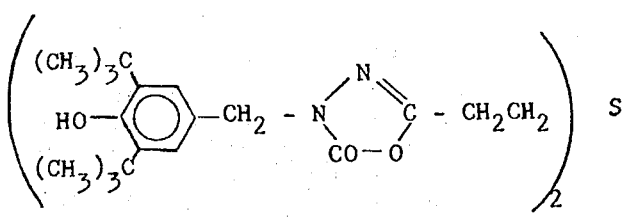

If, in Example 12, 5-ethoxy-1,3,4-thiadiazol-2-one is replaced by the equivalent amount of 2,2'-di-[2-oxo-1,3,4-oxadiazolin-5-yl]-diethyl sulphide and otherwise the same procedure is followed, 2,2'-di-[3-(3,5-di-t.-butyl-4-hydroxybenzyl)-2-oxo-1,3,4-oxadiazolin-5-yl]-diethyl sulphide is obtained.

EXAMPLE 15

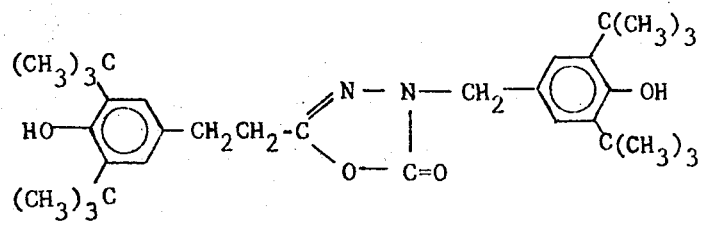

31.8 g of 5-(3,5-di-tert.-butyl-4-hydroxyphenylethyl)-1,3,4-oxadiazol-2-one (0.1 mol) and 36.9 g of N,N-diethyl-dithiocarbamic acid (3,5-di-tert.-butyl-4-hydroxybenzyl) ester (0.1 mol) are suspended in 400 ml of ethanol, 4.0 g of sodium hydroxide in 40 ml of water are added and the mixture is heated to 70°C for 10 hours, whilst stirring. A clear, yellowish-coloured solution results. After cooling, the reaction mixture is neutralised with acetic acid and 500 ml of water are added. The resulting oily product which separates out is separated from the water phase and dried with sodium sulphate. On treatment with hexane, the substance slowly becomes crystalline. The crude product is isolated, recrystallised from hexane and dried.

3-(3,5-Di-t.-butyl-4-hydroxybenzyl)-5-(3,5-di-t.-butyl-4-hydroxyphenylethyl)-1,3,4-oxadiazol-2-one (stabiliser No. 10), thus obtained, has a melting point of 115°C.

EXAMPLE 16

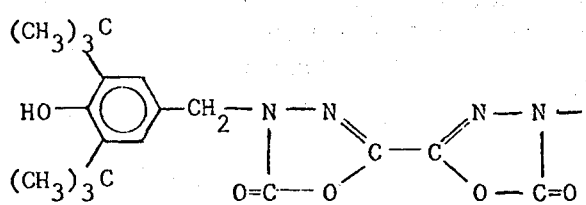 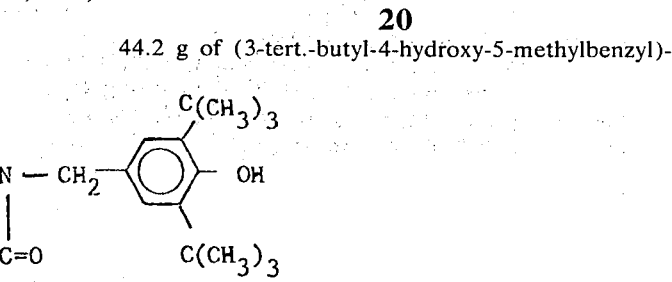

17.0 g of di-(2-oxo-1,3,4-oxadiazolin-5-yl) (0.1 mol) and 52.7 g of 3,5-di-t.-butyl-4-hydroxybenzyl-dimethylamine (0.2 mol) in 100 ml of toluene and 50 ml of dimethylformamide are kept at the reflux temperature for 15 hours whilst passing nitrogen through the mixture. The reaction takes place with elimination of dimethylamine. The solvent is then evaporated off in vacuo and the amorphous residue is digested with methanol, whereupon a white, powdery precipitate results. The product is filtered off, washed with a little methanol and dried. Di-[3-(3,-5-di-tert.-butyl-4-hydroxybenzyl)-2-oxo-1,3,4-oxadiazolin-5-yl] (stabiliser No. 11), thus obtained, melts at 260°C.

EXAMPLE 17

If, in Example 16, di-(2-oxo-1,3,4-oxadiazolin-5-yl) is replaced by an equivalent amount of 1,4-di-(2-oxo-1,3,4-oxadiazolin-5-yl)-n-butane and otherwise the same procedure is followed, 1,4-di-[3-(3,5-di-tert.-butyl-4-hydroxybenzyl)-2-oxo-1,3,4-oxadiazolin-5-yl]-n-butane (stabiliser No. 12) of melting point 190°C is obtained.

EXAMPLE 18

If, in Example 16, di-(2-oxo1,3,4-oxadiazolin-5-yl) is replaced by an equivalent amount of 1,8-di-(2-oxo-1,3,4-oxadiazolin-5-yl)-n-octane and otherwise the same procedure is followed, 1,8-di-[3-(3,5-di-tert.-butyl-4-hydroxybenzyl)-2-oxo-1,3,4-oxadiazolin-5-yl]-n-octane (stabiliser No. 13) of melting point 142°C is obtained.

EXAMPLE 19

If, in Example 16, di-(2-oxo-1,3,4-oxadiazolin-5-yl) is replaced by an equivalent amount of 1,2-di-(2-oxo-1,3,4-oxadiazolin-5-yl)-ethylene and otherwise the same procedure is followed, 1,2-di-[3-(3,5-di-tert.-butyl-4-hydroxybenzyl)-2-oxo-1,3,4-oxadiazolin-5-yl]-ethylene (stabiliser No. 14) of melting point 263°C is obtained.

EXAMPLE 20

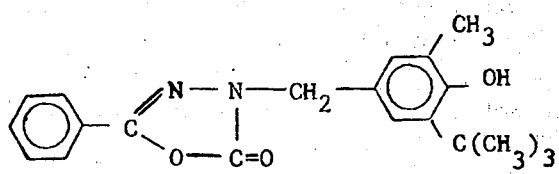

44.2 g of (3-tert.-butyl-4-hydroxy-5-methylbenzyl)-dimethylamine (0.2 mol) and 32.4 g of 5-phenyl-1,3,4-oxadiazo-2-one (0.2 mol) are dissolved in 300 ml of dimethylformamide and 0.2 g of lithium amide is then added. The mixture is stirred for 2 hours at 70°C and then for 17 hours at 90°C. After cooling, a little insoluble matter is filtered off and the filtrate is stirred into 2 liters of water. The solid which has precipitated is filtered off and recrystallised from methanol. 3-(3-Tert.-butyl-4-hydroxy-5-methylbenzyl)-5-phenyl-1,3,4-oxadiazol-2-one (stabiliser No. 15) thus obtained, melts at 152°C after drying in vacuo.

EXAMPLE 21

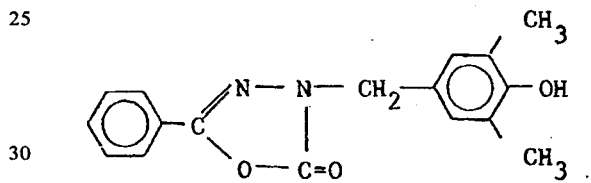

40.5 g of 5-phenyl-1,3,4-oxadiazol-2-one (.25 mol) and 71 g of N,N-diethyl-dithiocarbamic acid (4-hydroxy-3,4-dimethylbenzyl) ester (0.25 mol) are dissolved in 500 ml of isopropanol at 60°C. After dropwise addition of 10 g of sodium hydroxide in 100 ml of water, the mixture is stirred for 9 hours at 60°C. The solvent is then largely evaporated off, the yellow residue is dissolved in acetonitrile, insoluble matter is filtered off and the mother liquor is again evaporated. The residue, which crystallises slowly, is recrystallised from methanol. 3-(3,5-Dimethyl-4-hydroxybenzyl)5-phenyl-1,3,4-oxadiazol-2-one (stabiliser No. 16) of melting point 135°C is thus obtained.

EXAMPLE 22

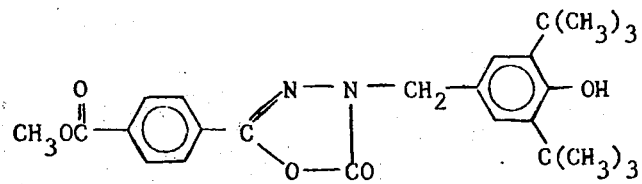

22.0 g of 5-(4-carbomethoxyphenyl)-1,3,4-oxadiazol-2-one 0.1 mol) are suspended in 300 ml of dimethylformamide and a 50% strength solution of 25.5 g of 3,5-di-t.-butyl-4-hydroxybenzyl chloride (0.1 mol) in toluene is added. 10.5 g of triethylamine (approx. 0.1 mol) are then added, whilst stirring, and the reaction mixture is heated to 30°–40°C for several hours. In the course thereof, the starting material dissolves whilst the triethylamine hydrochloride formed precipitates.

The latter is separated off and the reaction solution is poured onto about 600 ml of ice water. The reaction product precipitates in an amorphous form and solidifies to crystals. These are filtered off, digested with a little cold methanol and purified by recrystallisation from ligroin. The resulting 3-(3,5-di-t.-butyl-4-hydroxybenzyl)-5-(4-carbomethoxy-phenyl)-1,3,4-oxadiazol-2-one forms colourless crystals which melt at 141°C. (Stabiliser No. 17).

EXAMPLE 23

100 parts of polypropylene (melt index 2.6 g/10 minutes, 230°C/2,160 g) are thoroughly mixed with 0.2 part of one of the additives listed in Table 2 below, for 10 minutes, in a shaking apparatus.

The resulting mixture is kneaded in a Brabender plastograph at 200°C for 10 minutes and the composition thus obtained is then pressed in a platen press at 260°C platen temperature to give 1 mm thick sheets from which strips 1 cm wide and 17 cm long are punched.

The activity of the additives introduced into the test strips is tested by heat aging in a circulating air oven at 135°C, using an additive-free test strip for comparison. Three test strips of each formulation are employed for this purpose. The incipient decomposition of the test strip, readily recognisable from the complete embrittlement, is defined as the end point. The results are quoted in days.

Table 2

| Stabiliser No. | Days to reach incipient decomposition at 135°C |
| --- | --- |
| Without additive | 1 |
| 1 | 45 |
| 3 | 10 |
| 5 | 10 |
| 7 | 10 |
| 9 | 20 |
| 10 | 121 |
| 11 | 13 |
| 12 | 100 |
| 13 | 14 |
| 14 | 88 |

EXAMPLE 24

The test specimens described in Example 21 are additionally tested for colour stability, in particular:
a. After incorporation (Table 3, column 2).
b. After 500 hours exposure in a Xenotest apparatus of Messrs. Hanau (Table 3, column 3).
c. After 1 week's treatment with boiling water (Table 3, column 4).

The assessment was made using an empirical colour scale in which 5 denotes colourless, 4 denotes a just perceptible, slight discolouration and 3, 2, 1 and <1 denote progressively stronger discolouration.

Table 3

| Stabiliser No. | Colour assessment on scale of 1–5 | | |
| --- | --- | --- | --- |
| | After incorporation | After exposure | Boiling water, 1 week |
| Without additive | 5 | 5 | 4–5 |
| 1 | 4–5 | 4–5 | 4–5 |
| 3 | 4–5 | 5 | 4–5 |
| 5 | 4–5 | 5 | 3–4 |
| 7 | 4 | 4 | 4 |
| 9 | 4–5 | 4–5 | 4 |
| 10 | 4–5 | 4–5 | 4–5 |
| 11 | 4 | 5 | 4 |
| 12 | 4 | 5 | 4 |
| 13 | 5 | 5 | 4 |
| 14 | 4–5 | 5 | 5 |

EXAMPLE 25

100 parts of polypropylene (melt index 2.6 g/10 minutes, 230°C/2,160 g) are thoroughly mixed with 0.1 part of one of the additives listed in Table 4 below and 0.3 part of dilauryl thiodipropionate for 10 minutes in a shaking apparatus; in other respects, the procedure followed is as in Example 17. A test strip which only contains 0.3 part of dilauryl thiodipropionate is used for comparison.

Table 4

| Stabiliser No. | Days to reach incipient decomposition | |
| --- | --- | --- |
| | 149°C | 135°C |
| Comparison | 5 | 11 |
| 1 | 28 | 121 |
| 2 | 12 | 36 |
| 3 | 12 | 45 |
| 4 | 15 | 60 |
| 5 | 11 | 49 |
| 6 | 11 | 44 |
| 7 | 10 | 90 |
| 8 | 15 | 55 |
| 9 | 37 | 127 |
| 10 | 29 | 134 |
| 11 | 22 | 65 |
| 12 | 43 | 164 |
| 15 | 12 | 40 |
| 16 | 12 | 40 |
| 17 | 10 | 40 |
| 13 | 19 | 77 |
| 14 | 45 | 170 |

EXAMPLE 26

The test specimens described in Example 23 are additionally tested for colour stability, in particular:
a. After incorporation (Table 5, column 2).
b. After 500 hours exposure in a Xenotest apparatus of Messrs. Hanau (Table 5, column 3).
c. After 1 week's treatment with boiling water (Table 5, column 4)

For Table 5, an empirical colour scale was used, in which 5 denotes colourless, 4 denotes a just perceptible, slight discolouration and 3, 2, 1 and <1 denote progressively stronger discolouration.

Table 5

| Stabiliser No. | Colour assessment on scale of 1–5 | | |
| --- | --- | --- | --- |
| | After incorporation | After exposure | Boiling water, 1 week |
| 1 | 5 | 4–5 | 4–5 |
| 2 | 5 | 4–5 | 4–5 |
| 3 | 5 | 5 | 4–5 |
| 4 | 4–5 | 4–5 | 4–5 |
| 5 | 5 | 5 | 4 |
| 6 | 5 | 4–5 | 4–5 |
| 7 | 5 | 4–5 | 4–5 |
| 8 | 4–5 | 4–5 | 4–5 |
| 9 | 5 | 5 | 4–5 |
| 10 | 5 | 4–5 | 4–5 |
| 11 | 4–5 | 5 | 4–5 |
| 12 | 5 | 5 | 4–5 |
| 15 | 5 | 5 | 4–5 |
| 16 | 5 | 5 | 5 |
| 17 | 4–5 | 4–5 | 4–5 |
| 13 | 4–5 | 5 | 4–5 |
| 14 | 5 | 5 | 5 |

EXAMPLE 27

Assessment of the resistance to "gas fading"

A piece of cotton fabric is impregnated with a 1% strength solution of one of the additives from Table 6 below and is then dried. The piece of fabric treated in this way is exposed to the flue gases from a series of natural gas burners for 1 hour at a temperature of 100°C in a closed chamber. The piece of fabric is then extracted with a mixture of 100 ml of dimethylacetamide and 1 ml of piperidine. The intensity of the colouration (yellow in most cases) of the resulting solution is treated as a measure of the resistance to gas fading of the additive investigated.

For Table 6, an empirical colour scale was used, in which 5 denotes colourless, that is to say very good resistance to gas fading, 4 denotes a just perceptible slight discolouration and 3, 2 and 1 denote progressively stronger discolouration.

Table 6

| Stabiliser No. | Colour assessment on scale of 1–5, after gas fading |
|---|---|
| 1 | 5 |
| 2 | 5 |
| 3 | 4–5 |
| 8 | 4–5 |
| 9 | 5 |
| 11 | 5 |
| 12 | 4–5 |

EXAMPLE 28

Stabilisation of polyamide 6

The additives listed in Table 7 are sprinkled dry, at a concentration of 0.5%, onto dried polyamide 6 granules (relative viscosity of a 1% strength solution in concentrated sulphuric acid: 2.9), and the sprinkle-coated mixtures were regranulated on a single-screw extruder at 260°C. 0.3 mm thick pressed films are then produced from the granules, again at 260°C, and 1 cm wide test strips are punched from these pressed films.

The activity of the additives introduced into these test specimens is tested by heat aging in a circulating air oven at 165°C. The thermo-oxidative degradation of the material during heat aging is followed by periodically measuring the relative viscosity of a 1% strength solution in 96% strength sulphuric acid, determining the time after which the relative viscosity falls from 2.9 to a value of 2.0. (Table 7).

Table 7

| Stabiliser No. | Heat aging time at 165°C for a decrease in the relative solution viscosity from 2.9 to 2.0, in hours |
|---|---|
| Without additive | 5 |
| 1 | 17 |
| 5 | 21 |
| 7 | 18 |
| 9 | 25 |
| 12 | 27 |

EXAMPLE 29

Stabilisation of an ethylene-propylene rubber 100 parts of unstabilised ethylene-propylene rubber are homogenised for 10 minutes with 0.1 part of one of the stabilisers indicated in Table 8, in a Brabender plastograph, equipped with a type 50 EC roller kneader, at 150°C and 60 revolutions/minute. The mixtures stabilised in this way are pressed in a platen press at 120°C for 5 minutes to give 1 mm thick sheets. The unstabilised rubber sheet which serves for comparison is produced in the same manner.

The criterion used for the protective action of the stabilisers incorporated is the gel content determined after storage in air at elevated temperatures. For this purpose, the test samples obtained as above are kept at 100°C on an aluminium support in a circulating air oven and their gel content is examined periodically, being determined as follows: About 1 g of the samples is cut into pieces of size approx. 3×3×1 mm and these are dissolved overnight in 100 ml of n-hexane at room temperature. These solutions are filtered through glass wool, the gel particles retained by the glass wool are rinsed with 3 times 20 ml of n-hexane and the filtered solutions are evaporated to dryness and dried to constant weight. The gel content of a sample is then obtained from the following calculation:

$$\text{Gel content in \%} = \frac{E - A}{E} \cdot 100$$

In this equation, E = total weight of the sample examined and A = weight of the dissolved portion of the sample examined.

The time after which the gel content of the stabilised sample reaches 15% is defined as the measure of the activity of the stabiliser. The results are quoted in hours.

Table 8

| Stabiliser No. | Hours to reach a gel content of 15% |
|---|---|
| Without stabiliser | 500 |
| 1 | 2,400 |
| 7 | 3,100 |
| 9 | 2,900 |
| 12 | 3,350 |

EXAMPLE 30

Stabilisation of a polyurethane 0.25 part of one of the additives from Table 9 below and 0.25 part of 2-(2'-hydroxy-5'-methylphenyl)-benztriazole are dissolved cold in 100 parts of a 25% strength polyurethane solution (ESTANE 5707 of Messrs. Goodrich; solvent dimethylformamide-acetone, 1:1).

Approx. 400μ thick films of these solutions are spread on a glass plate by means of a film spreader; these dry, after approx. 10 minutes drying in circulating air at 140°C, to give films of final thickness 100μ. Accordingly, the stabilisers are present in the films at a concentration of 1.0%. Samples of these films are exposed on a white card background in a Xenotest apparatus until an incipient visually perceptible yellowing is reached. The results in Table 9 are quoted in hours.

Table 9

| Stabiliser No. | Exposure time in the Xenotest apparatus required to reach visible yellowing |
|---|---|
| Without stabiliser | 200 |
| 4 | 250 |
| 10 | 300 |

What we claim is:
1. A compound of the formula

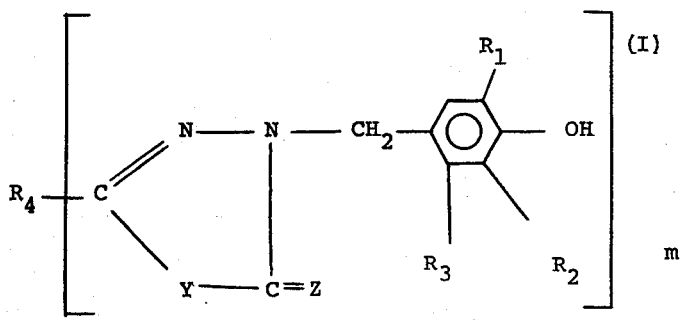

wherein $R_1$ is alkyl with 1 to 8 carbon atoms, $R_2$ is hydrogen or alkyl with 1 to 8 carbon atoms, $R_3$ is hydrogen or methyl, $R_4$, if $m = 1$, is hydrogen; alkyl with 1 to 18 carbon atoms; a group of the formula $C_xH_{2x+1}$—Q—$C_yH_{2y}$—, wherein Q is an oxygen or sulphur atom and $x$ and $y$ are integers of which the sum is 2 to 20; cyclohexyl, cyclooctyl, or methylcyclohexyl; alkylthio or alkyloxy with 1 to 18 carbon atoms; benzyl, phenylethyl, phenylpropyl, diphenylmethyl, benzyl; phenylethyl or phenylpropyl substituted by up to 2 alkyls of 1 to 4 carbon atoms each and/or by hydroxyl; unsubstituted phenyl or naphthyl; phenyl substituted by up to 2 substituents selected from halogen, hydroxyl, alkyl with up to 12 carbon atoms, alkoxy with 1 to 12 carbon atoms, or alkoxycarbonyl with 2 to 5 carbon atoms; or a group

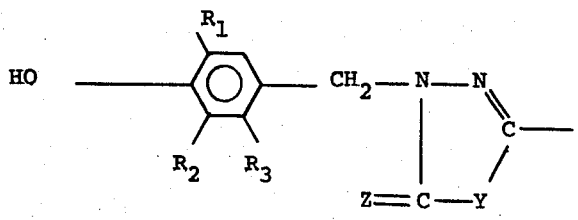

wherein $R_1$, $R_2$ and $R_3$ have the above meaning and $y$ and $z$ independently of one another are oxygen or sulphur, or, if $m=2$, $R_4$ is alkylene of 1 to 8 carbon atoms, a group of the formula —$C_xH_{2x}$—Q—$C_yH_{2y}$—, wherein Q is an oxygen or suphur atom and $x$ and $y$ are integers of which the sum is 2 to 4, phenylene, diphenylene, or naphthylene, Y and Z independently of one another are oxygen or sulphur and $m$ is the number 1 or 2.

2. A compound according to claim 1, wherein $R_1$ is alkyl with 1 to 8 carbon atoms, $R_2$ is hydrogen, or alkyl with 1 to 8 carbon atoms, $R_3$ is hydrogen or methyl, $R_4$, if $m=1$, is hydrogen, alkyl with 1-18 carbon atoms, a group of the formula $C_xH_{2x}{}^+{}_1$—Q—$C_yH_{2y}$—, wherein Q is an oxygen or sulphur atom and $x$ and $y$ are integers of which the sun is 2 to 20, cyclohexyl, alkylthio or alkyloxy with 1-18 carbon atoms, benzyl, phenylethyl, phenylpropyl, diphenylmethyl, or benzyl, phenylethyl or phenylpropyl substituted by up to 2 alkyls of 1 to 4 carbon atoms each and/or by hydroxyl, unsubstituted phenyl or naphthyl, phenyl substituted by up to 2 substituents selected from halogen, hydroxyl, alkyl with 1 to 12 carbon atoms, alkoxy with 1 to 12 carbon atoms, or alkoxycarbonyl with 2 to 5 carbon atoms, or a group

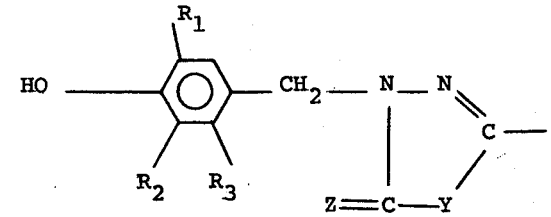

wherein $R_1$, $R_2$, and $R_3$ have the above meaning and Y and Z independently of one another are oxygen or sulphur, or, if $m=2$, $R_4$ is alkylene with 1 to 8 carbon atoms, a group of the formula —$C_xH_{2x}$—Q—$C_yH_{2y}$—, wherein Q is an oxygen or sulphur atom and $x$ and $y$ are integers of which the sum of 2 to 4, phenylene, diphenylene, or naphthylene, Y and Z independently of one another are oxygen or sulphur and $m$ is the number 1 or 2.

3. A compound according to claim 1 wherein $R_1$ and $R_2$ independently of one another are alkyl with 1 to 5 carbon atoms, $R_3$ is hydrogen, $R_4$, if $m=1$, is alkyl with 1 to 18 carbon atoms, a group of the formula $C_xH_{2x}{}^+{}_1$—S—$C_yH_{2y}$—, wherein $x$ and $y$ are integers of which the sum is 2 to 14 carbon atoms, benzyl, phenylethyl or phenylpropyl which is substituted by 2 alkyl groups with 1 to 4 carbon atoms and by one hydroxyl group, unsubstituted phenyl, phenyl substituted by a substituent selected from chlorine, hydroxyl, alkyl with 1 to 4 carbon atoms, or alkoxycarbonyl with 2 to 3 carbon atoms, or a group

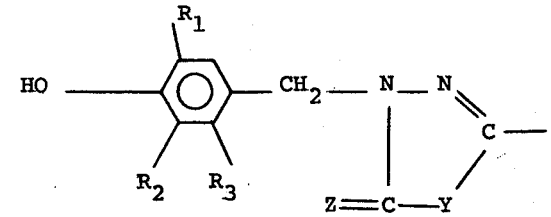

in which $R_1$, and $R_3$ have the above meaning and Y and Z independing of one another are oxygen or sulphur, or , if $m=2$, $R_4$ is alkylene with 2 to 4 carbon atoms, a group of the formula —$C_xH_{2x}$—Q—$C_yH_{2y}$—, wherein Q is a sulphur atom and $x$ and $y$ are integers of which the sum is 2 to 4, phenylene, Y and Z independently of one another are oxygen or sulphur and $m$ is the number 1 or 2.

4. A compound according to claim 3, wherein $R_1$ and $R_2$ are isopropyl or tertiary butyl and $R_3$, $R_4$, Y, Z and $m$ are as defined in claim 3.

5. The compound 3-[3,5-di-tert.-butyl-4-hydroxybenzyl]-5-phenyl-1,3,4-oxadiazol-2-one.

6. The compound 1,4-di-[3-(3,5-di-tert.-butyl-4-hydroxybenzyl)-2-oxo-1,3,4-oxadiazolin-5-yl]-butane.

* * * * *